United States Patent [19]
Nilsson

[11] Patent Number: 5,339,817
[45] Date of Patent: Aug. 23, 1994

[54] SYSTEM AND A METHOD FOR MEASUREMENT AND PRESENTATION OF FLUID FLOW MOVEMENTS, PARTICULARLY THE FLOW OF BLOOD THROUGH A BODY ORGAN

[76] Inventor: Gert Nilsson, Lövsbergsvägen 13, S-582 69 Linköping, Sweden

[21] Appl. No.: 852,145
[22] PCT Filed: Oct. 30, 1990
[86] PCT No.: PCT/SE90/00705
 § 371 Date: Apr. 30, 1992
 § 102(e) Date: Apr. 30, 1992
[87] PCT Pub. No.: WO91/06244
 PCT Pub. Date: May 16, 1991

[30] Foreign Application Priority Data
 Oct. 31, 1989 [SE] Sweden ............... 8903641-2
 Jul. 19, 1990 [SE] Sweden ............... 9002467-0

[51] Int. Cl.$^5$ ............................................. A61B 6/00
[52] U.S. Cl. ........................... 128/664; 128/665; 128/666; 128/691
[58] Field of Search .......................... 128/664–667, 128/691; 351/206–208; 354/62

[56] References Cited

U.S. PATENT DOCUMENTS

| | | | |
|---|---|---|---|
| 3,511,227 | 2/1967 | Johnson | 128/666 |
| 4,495,949 | 1/1985 | Stoller | 128/664 |
| 4,579,430 | 4/1986 | Bille | 128/633 |
| 4,590,948 | 5/1986 | Nilsson | |
| 4,596,254 | 6/1986 | Adrian et al. | |
| 4,743,107 | 5/1988 | Aizu et al. | 128/691 |
| 4,862,894 | 9/1989 | Fujii | |
| 4,979,818 | 12/1990 | Kobayashi | 128/691 |

FOREIGN PATENT DOCUMENTS

| | | | |
|---|---|---|---|
| 0389120 | 9/1990 | European Pat. Off. | 128/666 |
| 0488614 | 6/1992 | European Pat. Off. | 128/691 |
| 2531854 | 2/1984 | France | 128/666 |
| 9011044 | 3/1990 | World Int. Prop. O. | |

OTHER PUBLICATIONS

Nilsson et al., Medical & Biological Engineering & Computing, Jan. 1990, pp. N18–N19.
Wunderlich et al., Rev. Sci. Instrum., vol. 51, No. 9, Sep. 1980, pp. 1258–1262.

*Primary Examiner*—Lee S. Cohen
*Assistant Examiner*—Brian L. Casler
*Attorney, Agent, or Firm*—Browdy and Neimark

[57] ABSTRACT

The invention is directed to a system for the measurement and presentation of flow movements in a fluid to determine blood perfusion in superficial blood vessels of a body organ. The system includes a laser light source (1) generating a laser beam, apparatus for directing the laser beam onto a body part to be examined and for guided movement of the beam over the body part. The beam is moved over the body part in a predetermined scanning pattern (8). The system further includes a receiving part for the beam reflected from the body part, and apparatus for detecting broadening of the frequency of a reflected light beam caused by a Doppler effect. This results in measuring the magnitude of superficial blood circulation in the body part (5) at points scanned by the beam.

14 Claims, 4 Drawing Sheets

SYSTEM AND A METHOD FOR MEASUREMENT AND PRESENTATION OF FLUID FLOW MOVEMENTS, PARTICULARLY THE FLOW OF BLOOD THROUGH A BODY ORGAN

FIELD OF INVENTION

The present invention relates to a system and to a method for the measurement and presentation of flow movements in a fluid, and particularly for determining the magnitude of blood perfusion through the superficial blood vessels of a body organ. The system includes a laser beam generating source, means for directing the laser beam onto the part of the body to be examined and also to control the movement of the laser beam over said body part in accordance with a predetermined scanning pattern, and means for receiving part of the laser beam reflected from said body part.

BACKGROUND OF THE INVENTION

The invention is based on the application of the known laser-Doppler-technique for measuring the superficial circulation of blood in cutaneous tissue. This technique is described, for instance, in U.S. Pat. No. 3,511,227, U.S. Pat. No. 4,109,647, SE 419 678 and in the articles "In Vivo Evaulation of Microcirculation by Coherent Light Scattering", Stern N. D., Nature Vol. 254, pages 56–58, 1975; "A New Instrument for Continuous Measurement of Tissue Blood Flow by Light Beating Spectroscopy", Nilsson, G. E., Tenland T. and Öberg P. Å., IEE trans. BME-27, pages 12–19, 1980, and "Evaulation of a Laser Dopper Flow Meter for Measurement of Tissue Blood Flow", Nilsson G. E., Tenland T. and Öberg P. Å., IEE trans. BME-27, pages 597–604, 1980. In principle, this technique involves directing a laser beam onto a part of the tissue and receiving, with the aid of an appropriate photodetector, a part of the light scattered and reflected by that part of the tissue irradiated by the laser beam. As a result of the Doppler effect, the frequency of the reflected and scattered light will be broadened and the light will thus have a frequency spectrum which is broader than the original laser beam, this broadening of the light frequency being due to the influence of the movement of blood cells in the superficial part of the irradiated tissue. The extent to which the frequency is broadened and the light intensity within different parts of this broader frequency spectrum constitute a measurement of the magnitude of superficial blood circulation in the irradiated part of the tissue examined and can be determined or evaluated by appropriate processing of the photodetector output signal.

An instrument for visually presenting blood flow is known from U.S. Pat. No. 4,862,894. In this known instrument, the reflected laser light is detected by a line sensor consisting of a plurality of light receiving elements which emit successively signals that are converted and stored in a memory. A microprocessor makes calculations based on these stored signals.

According to U.S. Pat. No. 4,862,894, the reflected Doppler signal is evaluated by measuring the amplitude of the signal at time t and comparing the result with the amplitude of the signal at time $t+\Delta t$. Thus, the amplitude values of the Doppler signal are detected by this method, whereas the frequency content of the signal is completely ignored. However, the signal processing technique and the use of the algorithm described in U.S. Pat. No. 4,862,894 enable the technique for scanning the measurement area described in this Patent Specification to be used.

Under some conditions, the signal processing technique described in U.S. Pat. No. 4,862,894 will result in erroneous evaluation of the blood flow in a body part, since the frequency content of the Doppler signal is a component which is necessary in order to describe the blood flow correctly. Perfusion is proportional to the product of the speed and concentration of red blood cells and it is not possible to evaluate perfusion or average speed unambiguously, solely by studying changes in the amplitude, as proposed in U.S. Pat. No. 4,862,894.

THE BASIC CONCEPT OF THE INVENTION

The present invention is based on a signal processing method in which both the magnitude and the frequency of the Doppler signal are detected, which is necessary in order to obtain a correct measurement of the blood perfusion. In order to be able to evaluate the Doppler signal, it is necessary to detect the signal over a period of sufficient duration to enable all frequencies in the signal to be detected. Accordingly, the laser beam is halted at each measurement point for a given time interval, the signal being measured continuously.

The present invention relates to a system for the measurement and visual presentation of the magnitude of the superficial blood circulation over an area of a body part, for instance over a complete hand or foot, or part of a hand or foot, or part of a leg. The superficial blood circulation can vary considerably within different regions of a body part, and the described system will therefore enable the cause of an illness or a healing process to be studied effectively. The inventive system includes a laser beam generating source, and means operative to direct the beam onto the body part to be examined and to move the beam over said body part in accordance with a determined scanning pattern. The system also includes means for receiving light reflected from said body part and for detecting the broadening in the frequency of the reflected light caused by the Doppler effect and for recording this broadening of the frequency for a large number of points along the scanning path as a measurement of the superficial blood circulation in said body part at said measurement points. The system also includes means for visually presenting on a colour screen the magnitude of the superficial blood circulation at the scanned points, with the use of mutually different colours for mutually different magnitude intervals of blood circulation.

Those measurement or scanning points on the examined part of the body at which no blood circulates, or where blood circulation is only very slight, will cause no broadening of the frequency of the reflected light received, or at most only a slight broadening of the frequency. Thus, it will be impossible, or extremely difficult, to distinguish these measurements or scanning points from those measurement or scanning points which lie outside the examined part of the body. This may make it difficult to interpret correctly the image of the superficial blood circulation in various regions of the body part examined on the colour screen.

This drawback is eliminated by one advantageous embodiment of the invention, in that an underlay on which the examined body part is placed is configured so as to be substantially non-reflective, i.e. is either transparent or light-absorbent. The signal obtained from the detector is analyzed in the signal processing unit, not only with respect to the broadening of the signal frequency, but also with respect to the absolute value of the intensity of the reflected light received by the detector. Since the underlay is substantially nonreflective, the light reflected at the measurement or scanning points located outside the examined body part will have a very low intensity. Because all measurement or scanning points whose light intensity lies beneath a predetermined limit value are marked with a unitary background colour, a readily interpreted image is obtained on the colour screen.

In the image producing system in which the laser beam scans the measurement object, the distance between measurement object point and detector surface will vary during scanning of said body part, and therewith also the angle of the reflected beam in relation to the detector. The so-called amplification factor of the system for the signal measured will therewith vary within one and the same image, which introduces distortion in the reproduction of the blood flow image.

In accordance with one preferred embodiment of the invention, compensation is made for those variations which occur in the output signal as a result of the relative position of the measurement point on the measurement object, so as to provide correct presentation of the measured flow values. This compensation enables a comparison to be made between different measurements, for instance will enable a healing process to be evaluated. It is also possible to present correctly an image of measurements made point by point on a systematically scannned surface.

BRIEF DESCRIPTION OF THE DRAWINGS

The invention will now be described in more detail with reference to the accompanying drawing, in which

FIGS. 2 A-D illustrate by way of example different Dopper signals reflected from a measurement point as a function of time;

DETAILED DESCRIPTION OF THE INVENTION

Figure 1:
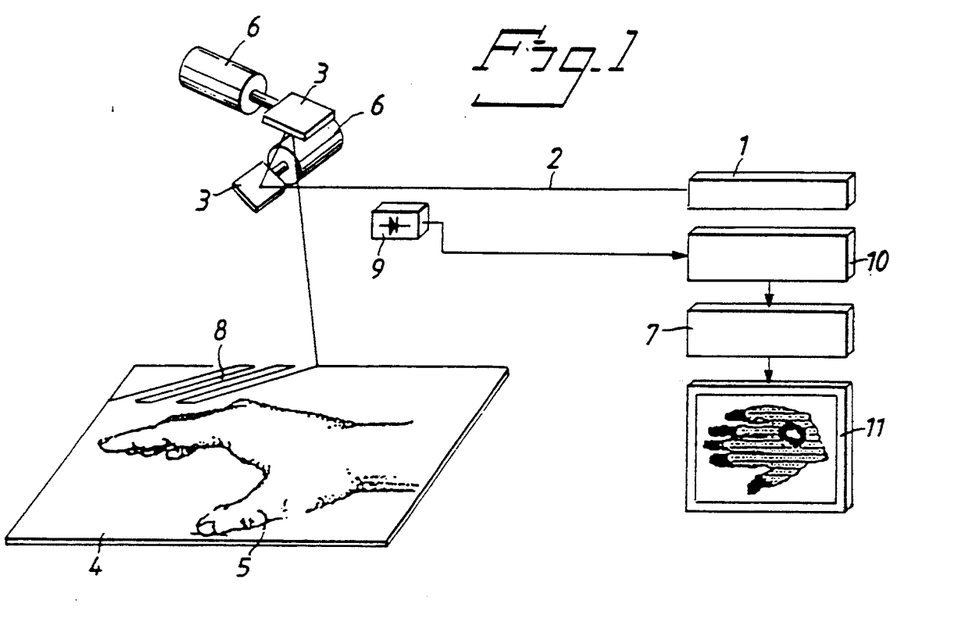
FIG. 1 is a schematic illustration of an exemplifying embodiment of a system for measuring and visually presenting the blood flow in a hand.

FIG. 1 illustrates schematically a system for the measurement and visual presentation of the superficial blood flow in a hand, and comprises a laser beam generating source 1 which produces a laser beam 2. The laser beam is directed onto an underlay 4, which supports the part of the body to be examined, with the aid of suitable optical elements, of which two mirrors 3 are shown in FIG. 1. The two mirrors can be swung by means of stepping motors 6 controlled by a computer 7, also illustrated schematically. The laser beam is caused to scan the underlay 4 and the body part 5 positioned thereon in accordance with a predetermined scanning pattern 8. Scanning movement of the laser beam 2 is preferably carried out in stages, so as to obtain a plurality of scanning or measuring points located sequentially along the scanning path 8.

If the laser beam 2 is assumed to have a diameter of 1 mm and the distance between the underlay 4, with the body part 5 resting thereon, and the scanning unit, i.e. the mirrors 3, is assumed to be about 20 cm, and the measurement points or scanning points are 3,600 in number, an area of $12 \times 12$ cm$^2$ can be covered with one single scanning procedure. When the laser beam 2 impinges on the body part 5, the beam will be scattered and reflected in the superficial tissue and therewith also to some extent by the blood cells in the superficial or cutaneous blood circulation in the measurement point concerned on said body part. Some of the scattered and reflected light is captured by a photodetector 9, of some suitable kind, and the photodetector output signal is delivered to a schematically illustrated signal processing unit 10. The frequency of the light received by the photodetector 9 is broader than the frequency of the original beam 2, this broadening of the frequency with respect to its magnitude and also with respect to the variations in light intensity in different parts of the frequency spectrum constitutes a measurement of the superficial blood circulation at the measurement point concerned on the body part 5 under examination. In order to be able to record both magnitude variations and frequency broadening in the reflected light, it is necessary for the laser beam to remain stationary at each measurement point for a period of time sufficient to enable all frequencies of the signal to be detected. It has been found that the laser beam must remain stationary for at least 20-30 milliseconds, in order to achieve satisfactory signal detection.

FIGS. 2 A-D illustrate Doppler signals which occur at different combinations of speed and concentration of red blood cells for one and the same perfusion or blood flow. This perfusion or blood flow is proportional to the product of the speed and the concentration of red blood cells in the measurement area. FIG. 2A-2D shows how the frequency of the Doppler signal is proportional to the mean speed of the blood cells, provided that the concentration is constant, whereas the magnitude for a given speed is related to the concentration.

Figure 2A:
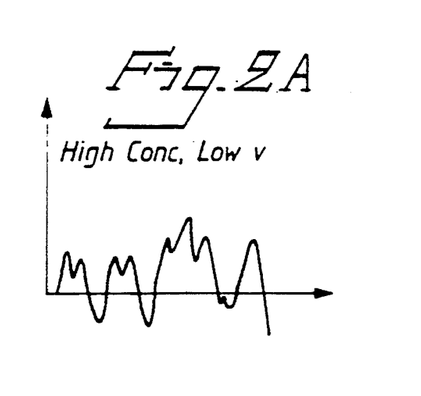
Figure 2B:
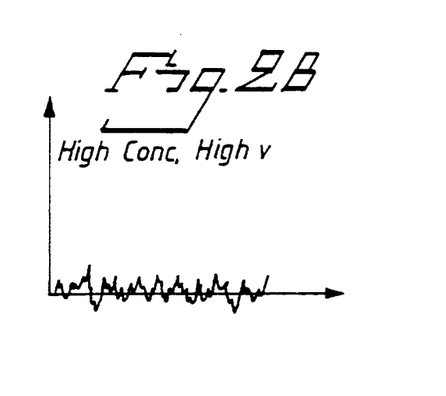
Figure 2C:
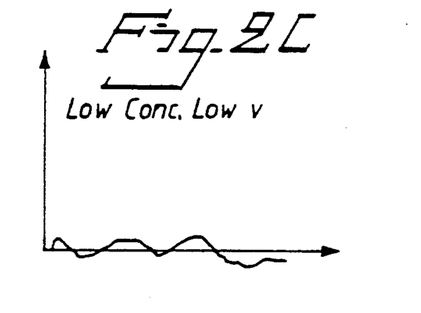

It will also be seen from FIG. 2A-2D that the magnitude decreases with increasing speed for a given concentration (see, for instance, FIGS. 2A and 2B). This is because the energy in the Doppler signal is now distributed over a larger frequency range (lower concentration for each speed interval).

Figure 2D:
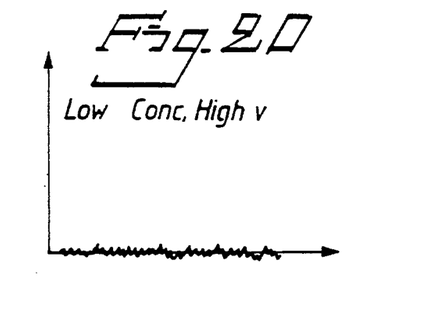

Thus, a high perfusion can be corresponded by a low signal magnitude when it is the speed component that increases and not the concentration. In actual fact, a reversed condition between magnitude and mean speed prevails, provided that perfusion is constant. Consequently, it is not possible to determine perfusion or mean speed unambiguously, by solely studying amplitude changes. FIGS. 2A and 2D illustrate a situation in which the mean flow rate is low in 2A and the concentration is also low 2A, and a comparison of these Figures will reveal that changes in signal amplitude at two mutually sequential measurements cannot be proportional to the mean speed (high mean speed in 2D and low amplitude and amplitude difference; low mean speed in 2A and high amplitude and amplitude difference).

Thus, a measurement of the magnitude of the superficial blood circulation is determined for each measurement point on the body part 5 being examined, by appropriate processing of the photodetector output signal in the signal processing unit 10. These measurement values are delivered to and stored in the computer 7 for all measurement points along the scanning pattern 8 of the laser beam 2. The computer 7 is connected to a colour monitor 11 on which an image of the body part 5 being examined is presented visually. Each individual measurement point in this image is shown in a specific colour corresponding to the range of magnitude within which the superficial blood circulation in corresponding measurement points on said body part lies. This produces a graphic, highly informative picture of the superficial blood circulation in the body part being examined. Because the absolute values of the superficial blood circulation in each measurement point on the body part being examined are stored in the computer 7, it is possible to select, with the aid of the computer 7, the different size intervals for the various colour codes in the image on the colour monitor 11, so as to obtain the best possible, informative visual presentation with each individual examination.

It will be evident from the aforegoing that at those measurement or scanning points on the examined body part 5 where blood circulation is non-existent or very low, there will be no broadening or a very slight broadening of the frequency of the reflected light received by the photodetector 9, and, consequently, it will be impossible or extremely difficult to distinguish these measurement or scanning points on the body part 5 from those measurement or scanning points which lie outside the examined body part 5. This may render it difficult to interpret correctly the image of the superficial blood circulation in different parts of the examined body part presented on the monitor 11.

This drawback is eliminated in accordance with one highly advantageous embodiment of the invention, by configuring the underlay 4, on which the examined body part 5 rests, in a manner such that the underlay will essentially reflect no light, i.e. by making the underlay either transparent or light absorbent, and by analyzing the photodetector output signal in the signal processing unit 10 solely with respect to the frequency broadening of said signal without taking into consideration its absolute value, i.e with respect to the intensity of the reflected light received by the photo-detector 9, and by storing in the memory of the computer 7 the intensity values of the reflected light received for each measurement or scanning point along the whole of the scanning pattern 8. Thus, subsequent to each scanning process, two "images" are found stored in the memory of the computer 7, of which "images" one represents the magnitude of the superficial blood circulation in each scanning or measurement point, and the other "image" represents the intensity of the light reflected from each scanning or measurement point. Since the underlay 4 is essentially non-reflective, it will be realized that this latter "image" presents a very low intensity of the light reflected from the measurement or scanning points which lie outside the examined body part. These two "images" stored in the computer 7 can be used to produce on the monitor 11 a visual presentation of an image or a picture in which all measurement or scanning points, i.e. picture pixels, which have a reflected light intensity beneath a predetermined limit value are marked with a unitary background colour, whereas only those measurement or scanning points, i.e. picture pixels, which have a reflected light intensity that lies above said limit value are marked with a colour representing a given size interval for the superficial blood circulation. The picture presented on the monitor in this way is far more informative and much more readily interpreted than is otherwise the case. Naturally, when producing the picture on the colour monitor, the magnitude of the aforesaid limit value of the reflected light intensity during which background colours are used can be selected in accordance with prevailing requirements.

Figure 3:
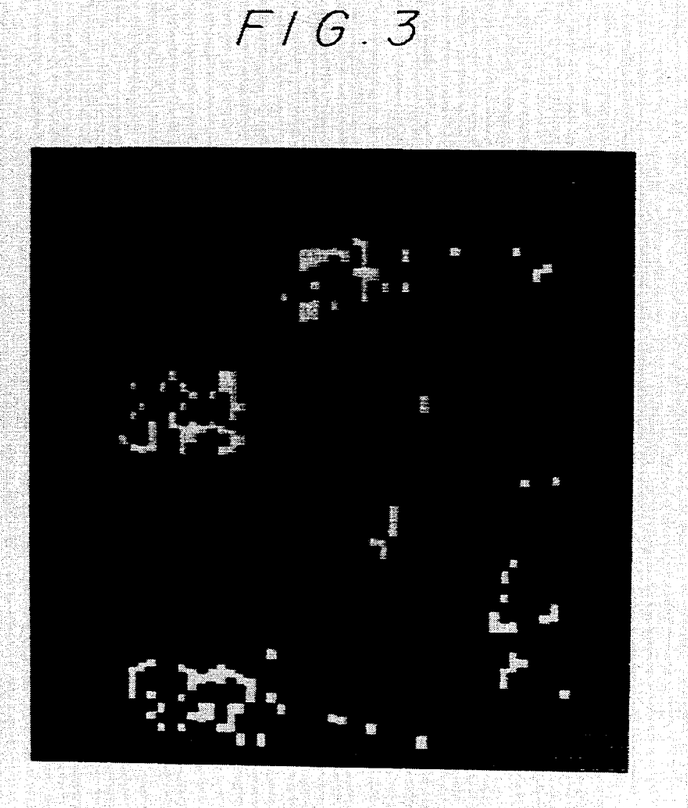
FIG. 3 illustrates by way of example a visual presentation of the superficial blood circulation of part of a hand, in accordance with the invention.

FIG. 3 is an exemplifying illustration of a picture (in black and white) produced in the aforedescribed manner and showing the superficial blood circulation in part of a hand. In this picture, the background, i.e. the area outside the outer contours of the hand, is marked with a mauve or purple colour, whereas the various size ranges of the superficial blood circulation in the hand are marked in sequence in black, blue, green, yellow and orange colours in the case of progressively greater superficial blood circulation. The hand examined in the illustrated example carried a ring on one finger, and the ring appeared on the picture as a black band over the finger concerned, while another finger was provided with an occlusion which cut-off the superficial or cutaneous blood circulation in the outermost part of said finger. This is shown clearly in the picture, where said outermost part of the finger concerned shows up black.

Figure 4:
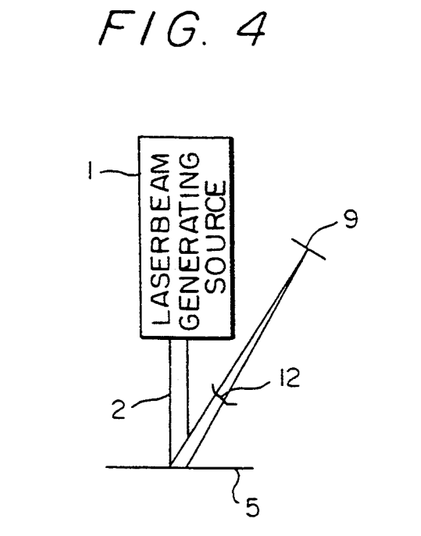
FIG. 4 illustrates schematically how a measurement object is visible from a detector included in an apparatus according to FIG. 1.

FIG. 4 illustrates the laser beam 2 directed onto the skin surface 5 where the flow of blood is to be measured, wherein a Doppler shift of certain photons in the laser beam takes place and gives rise to a frequency broadening and also in variations in the intensity of the light reflected. These variations in intensity are recorded with the aid of a photodetector 9, which is preferably located at a distance of about 20 cm from said skin surface, and are converted to a signal which is proportional to the blood flow.

Figure 5:
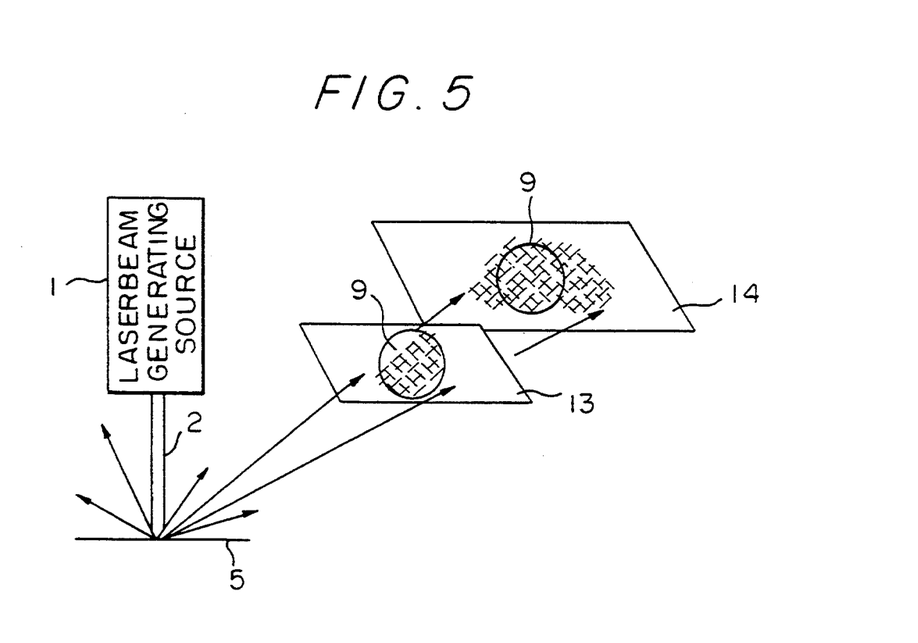
FIG. 5 illustrates schematically a speckle pattern reproduced at mutually different distances from the measurement object.
Figure 6:
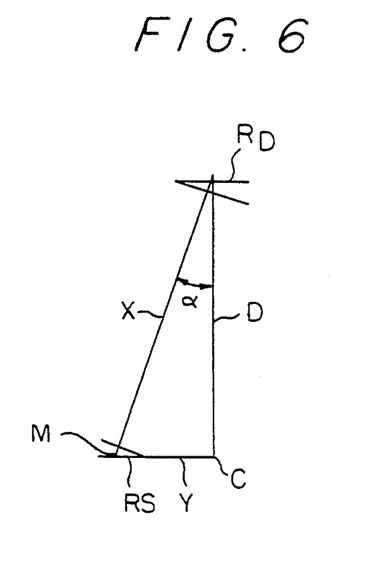
FIG. 6 illustrates schematically the relationships between different components of the FIG. 4 illustration.

When laser light is scattered in a medium, the scattered light consists of Doppler-broadened light, the intensity variations of which, mirrored for instance on a white screen, are represented by a so-called laser speckle, as illustrated in FIG. 5. When light emitted by a light source of given geometrical extension (such as the end of an optic fibre) is incident on a surface (such as the surface of a photodetector), there is formed a defraction pattern (speckle) whose appearance is contingent on the physical extension of the light source, the distance between the light source and the photodetector surface, and the wavelength of the light emitted. When the medium on which the light impinges is in motion, such as red blood cells which perfuse a tissue, this speckle will constantly undergo a phase shift, i.e. will be constantly in motion ("boil" in the technical jargon used). It is this pattern of movement which is detected by the photodetector 9 located at a given distance from the skin surface being examined, and which is converted to a signal which is proportional to the blood flow. The magnitude (fine structure) of the shifts in the speckle between dark and light fields on the detecting, photosensitive surface is designated the coherence area. Under certain, fixed conditions, the size of the coherence area depends on the distance between the measurement object 5 and the detector 9, see FIG. 6, in accordance with the formula:

$$A_{coh} = \lambda^2/\Omega \quad (1)$$

where $\lambda$ is the wavelength of the light and $\Omega$ is the solid angle 12 under which the light source is visible from the detector 9. FIG. 5 illustrates the reflection of a fine-grain speckle 13 onto a screen which lies relatively close to the measurement object 5, and also shows a coarse-grain speckle 14 reflected on a screen located at a relatively long distance from the measurement object 5.

Since the size of the solid angle 12 decreases with increasing distance between measurement object and detector, the size of the coherence area on the detector surface according to formula (1) is contingent on this distance. Since the area of the detector surface is constant, the number of coherence areas on the detector surface will be dependent on the distance between the measurement point on the measurement object 5 and the detector 9. A greater distance results in a smaller number of coherence areas on the detector surface, while conversely a smaller distance will result in a greater number of coherence areas.

When measuring blood flow with the aid of laser-Doppler-techniques, the so-called amplification factor, and therewith the size of the output signal, is contingent on the number of coherence areas which impinge on the detector surface. This relationship can be described in simple fashion by the formula:

$$\text{Output signal} = K_0 \times BF/N \quad (2)$$

where $K_0$ is an instrument constant, BF=the blood flow and N=the number of coherence areas on the detector surface. In conventional laser-Doppler-techniques based on light fibres, where the blood flow is detected pointwise at a constant distance between measurement object and detector surface and a constant solid angle 12 under which the light source at the fibre end is visible from the detector surface, the number of coherence areas will also be constant, according to the relationship of formula (1). The amplification factor of the system will not vary under these conditions, and, consequently, according to formula (2), the output signal will be directly proportional to the blood flow.

In other systems, on the other hand, the distance between measurement object and detector surface can vary between different measurement occasions, and, consequently, two images cannot be compared with respect to the absolute flow values. In the case of laser-Doppler-flow measuring techniques in which a body surface is scanned systematically and in stages, the solid angle, and therewith the number of coherence areas and the system amplification factor, will be contingent on the point on the measurement object at which backscattering of light occurs. This causes the amplification factor to vary within one and the same image and therewith introduces distortion in the reproduction of the flow image, unless these amplification factor variations can be corrected.

For the purpose of solving this distortion problem, an inventive method has been devised in which measurements and calculations are made of those amplification factor variations which occur at different measurement object points in relation to the amplification factor which occurs at an optimum measurement point. The size of the variations of the amplification factor, or the size of the variations in the number of coherence areas on the detector surface, is a function of the distance and the angle of the light beam incident on the measurement object point.

FIG. 6 illustrates the manner in which a system compensation factor can be measured and calculated. In FIG. 6:

$R_D$ = detector radius
$R_S$ = laser beam radius
D = perpendicular distance between detector plane and measurement object
C = measurement object point at D
X = distance of detector from the measurement point concerned
M = the measurement point concerned
Y = distance C - M
$\alpha$ = angle D - X In order to calculate the solid angle $\Omega$, i.e. the angle at which the light source on the measurement object is visible from the detector, the light propagation of the light source is compared with the total surface area of the sphere of radius X, i.e.:

$$\Omega = \frac{\pi R_s^2}{4\pi X^2} = \left(\frac{R_s}{2X}\right)^2$$

The size of the coherence area can now be calculated with the aid of formula (1).

$$A_{COH} = \frac{\lambda^2}{\Omega} = \lambda^2 \left(\frac{2X}{R_s}\right)^2 = \left(\frac{2\lambda X}{R_s}\right)^2$$

The number of coherence areas N which impinge on the detector surface can be calculated with the aid of the component of the detector radius perpendicular to the reflected beam, i.e. $R_D \cos \alpha$.

$$N = \frac{\pi (R_D \cos \alpha)^2}{A_{COH}} = \frac{\pi (R_D \cos \alpha)^2 R_S^2}{(2\lambda X)^2} =$$

$$\pi \left(\frac{R_D R_S \cos \alpha}{2\lambda X}\right)^2 = \pi \left(\frac{R_D R_S X \cos \alpha}{2\lambda X^2}\right)^2 =$$

$$\pi \left(\frac{R_D R_S D}{2\lambda(D^2 + Y^2)}\right)^2 = \pi \frac{R_D^2 R_S^2}{4\lambda^2} \left(\frac{D}{D^2 + Y^2}\right)^2$$

The compensation factor K can now be calculated by comparing the value of N for the optimum measurement point C.

$$N_c = \pi \frac{R_D^2 R_S^2}{(2\pi D)^2}$$

$$K = \frac{N}{N_c} = \left(\frac{D^2}{D^2 + Y^2}\right)^2$$

It will be evident from the formula by means of which the compensation factor is calculated that this factor can be calculated readily when 1) the perpendicular distance D between detector and measurement object is known, and
2) when it is known how the distance X between detector and measurement object changes as the laser beam moves over the measurement object, or in accordance with FIG. 6, when the value of the distance Y between the measurement object points C nearest the detector and the measurement point M concerned is known.

The perpendicular distance D is preferably measured by sending a short ultrasonic pulse onto the object 5 from an ultrasonic crystal 15 which is distance related to the detector plane. The time taken for this pulse to return to the crystal 15 and there detected is related linearly to the distance D. This distance can be calculated with knowledge of the speed of sound in air. For instance, by observing the number of steps through which the motors 6 are stepped forward as the laser beam 2 scans the measurement object 5 and storing this information, it is possible to calculate the distance to each measurement object point M and to use this calculation in the calculation of the compensation factor. When continuous motors are used for effecting rotary movement of the mirrors, there can be used instead a feedback system which is operative to detect the rotational positions of the mirrors and therewith the location of the measurement point concerned. In the case of the optimum measuring point C, the amplification factor will assume a typical value of 1 in the centre of the image, and will then increase successively out towards the perimeter edges of the image, where a typical value may be about 2. The compensation factor varies in a corresponding manner, from the optimum value 1 to a value of about 0.5.

Figure 7:
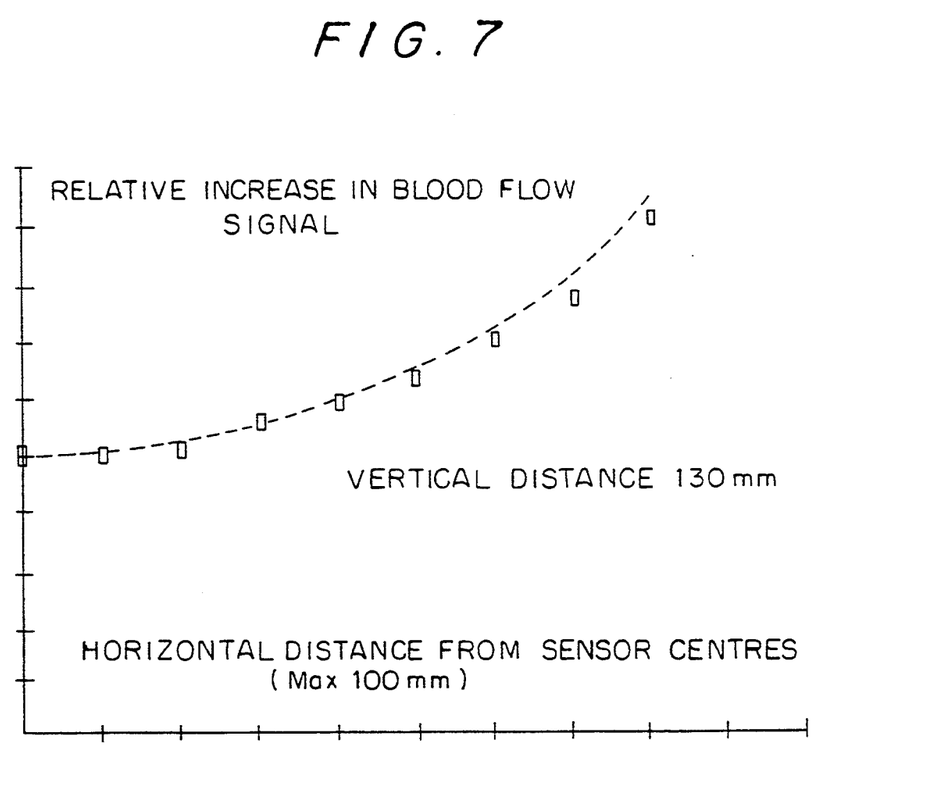
FIG. 7 is a diagram illustrating the flow values measured on a medium in uniform movement.

The result of an experiment performed in this regard is illustrated in FIG. 7, with the intention of exemplifying the above theoretical reasoning and in order to illustrate the significance of the amplification factor on the measurement result. In this experiment, the laser beam was swept over a medium in uniform motion (microspheres in solution), wherein the distance between detector and measurement object point varied during the beam scan over the object. As a result of these changes in distance, the solid angle 12 at which the light source is visible from the detector 9 also changed, and, consequently, the coherence area and therewith the number of coherence areas on the detector surface also varied. In consequence, a change in the value of the amplification factor was also observed during the scan. The smallest output signal is obtained when the measurement object point is located immediately beneath the detector, when Y=0. The number of coherence areas decreases when the measurement object point is located on the peripheral edge of the image, wherein the amplification factor increases. Since the measurement is concerned with uniform motion, a horizontal flow line should be read from the diagram in FIG. 7, if correction was made to the output signal with respect to the variation in the amplification factor. FIG. 7 shows that compensation for amplification factor variations is of great importance, since in the case of a non-compensated system erroneously high flow values, of up to 100%, are detected, particularly at the peripheral edges of the image. The Figure also includes the theoretically calculated amplification curve for which compensation shall be made with the aid of the compensation factor calculated in accordance with the aforegoing.

I claim:

1. A system for the measurement and presentation of flow movements in a fluid to determine blood perfusion in superficial blood vessels of a body organ, said system comprising:

a laser light source (1) generating a laser beam (2), means (3, 6) for directing said laser beam (2) onto a body part to be examined and for guided and stepwise movement of said laser beam over said body part (5) in accordance with a predetermined scanning pattern (8), wherein said means for directing said laser beam halts said laser beam at scanned points along said scanning pattern for a given time interval, means (9) for receiving part of said laser beam reflected from said body part, means (10, 7) for detecting over a large number of said scanned points broadening of a frequency of a received reflected light beam caused by a Doppler effect, wherein, said means for detecting measures the magnitude of superficial blood circulation in said body part (5) at said scanned points.

2. A system according to claim 1, wherein said system further comprises means (11) for producing on a colour screen a visual presentation of the magnitude of the superficial blood circulation at said scanned points, with the aid of different colours for mutually different blood circulating magnitude intervals.

3. A system according to claim 2, wherein said system further comprises an essentially non-reflective underlay (4) on which said body part (5) to be examined is placed, and said means (10, 7) for detecting, and said means for producing on a colour screen said visual presentation is constructed to mark on said colour screen the scanning points at which the intensity of the received reflected light does not exceed a given limit value with a colour which distinguishes from those colours used to mark the different magnitude intervals of said superficial blood circulation.

4. A system according to claim 3, wherein said underlay (4) is transparent or light absorbent.

5. A system according to claim 1, wherein said means (9) for receiving is a detector having a detector surface which defines a detector plane; and means are provide for detecting a distance (D,X) from the center of said detector plane to a measurement point (C) on the a body part positioned perpendicularly to said detector plane, or to one of said scanned points (M).

6. A system according to claim 5, wherein said means for detecting a distance (D,X) from the center of said detector plane and said measurement point (C) includes an ultrasonic crystal which is stationarily mounted in relation to said detector.

7. A method for measuring and presenting flow movements in a fluid, to determine blood perfusion in superficial blood vessels of a body organ, said method comprising the steps of:

directing a laser beam (2) generated by a laser beam source (1) onto a measurement object (5) in a form of a body organ which scatters and reflects the laser beam; receiving and detecting scattered and reflected light from said body organ in a detector (9) and detecting a broadening in frequency caused by a Doppler effect; compensating an output signal of the detected frequency broadening by use of a compensation factor (K) contingent on calculating a solid angle (12) within which said laser beam source is visible from said detector (9) at a point (M) on said measurement object (5) upon a pattern on which said laser beam has been directed.

8. A method according to claim 7, further comprising the step of:

calculating said compensation factor (K) contingent on a distance between said detector (9) and said point (M) and an angle of said reflected light in relation to a detector plane on said detector (9).

9. A method according to claim 8, further comprising the step of:

calculating said compensation factor (K) by measuring a perpendicular distance (D) between a center of said detector plane and a point (C) on aid measurement object (5), and by also measuring a distance (Y) between said point (C) and said point (M) on said measurement object (5).

10. A method according to claim 9, further comprising the steps of:

moving said laser beam (2) over said measurement object (5) in a determined scanning pattern, such that said detector (9) will receive and detect a light reflected from a large number of measurement points (M) along said scanning pattern; and determining said compensation factor (K) for each of said measurement points (M).

11. A method according to claim 10, further comprising the steps of:

moving said laser beam (2) with rotatable optic elements (3) which are rotated by stepping motors (6); determining said compensation factor (K) by measuring said perpendicular distance (D) between said center of said detector plane and the point (C) on said measurement object (5) and by measuring a number of steps moved by said stepping motors (6) from the position at which said laser beam was directed onto said point (C) to one of said measurement points (M).

12. A method according to claim 11, further comprising the steps of:

calculating the compensation factor (K) in accordance with a formula $$K = \left( \frac{D^2}{D^2 + Y^2} \right)^2,$$

where

D = the perpendicular distance (D) between said detector plane and said measurement object (5), and Y = a distance between the measurement object point (C) and D and said one of said measurement points (M).

13. A method according to claim 12, wherein said compensation factor (K) takes the value 1 at a prevailing measurement point of said measurement points (M) which corresponds to said measurement point (C) at said perpendicular distance from said center of said detector plane and decreases successively for other said measurement points (M) that are located further out towards peripheral edges of said measurement object (5).

14. A method according to claim 13, wherein said compensation factor (K) takes value between 1 and about 0.5.

* * * * *